United States Patent [19]

Tull, deceased et al.

[11] E Re. 31,429

[45] Reissued Oct. 25, 1983

[54] PROCESS FOR PREPARATION OF 9-(DIHALOBENZYL)ADENINES

[75] Inventors: Robert Tull, deceased, late of Metuchen, N.J.; George D. Hartman, Lansdale, Pa.; Leonard M. Weinstock, Belle Mead, N.J.

[73] Assignee: Merck & Co., Inc., Rahway, N.J.

[21] Appl. No.: 87,603

[22] Filed: Oct. 23, 1979

Related U.S. Patent Documents

Reissue of:

[64] Patent No.: 4,098,787
Issued: Jul. 4, 1978
Appl. No.: 768,235
Filed: Feb. 14, 1977

[51] Int. Cl.[3] ..... C07D 473/34

[52] U.S. Cl. ..... 544/277; 424/253

[58] Field of Search ..... 544/277; 424/253

[56] References Cited

U.S. PATENT DOCUMENTS 3,813,394 5/1974 Tensho et al. ..... 544/264
3,846,426 11/1974 Lira et al. ..... 544/277
4,100,159 7/1978 Zwann ..... 544/277
4,171,440 10/1979 Shinkai et al. ..... 544/277

OTHER PUBLICATIONS

Taylor et al., J. Chem. Soc., 36 3211-3217, (1971).
Shealey et al., J. Org. Chem., 27 2154–2160, (1962).
Hallstein et al. (Mutation Research 65 133-142 (1979).
Purchase et al. (British Journal of Cancer 37 873-903 (1978).

*Primary Examiner*—Nicholas S. Rizzo
*Attorney, Agent, or Firm*—David L. Rose; William H. Nicholson; Harry E. Westlake

[57] ABSTRACT

9-(Dihalobenzyl)adenines are prepared uncontaminated with other positional isomers in a series of mild transformations starting from 4,5,6-triaminopyrimidine and proceeding via 7-(N-formyl-N-dihalobenzyl)amino[1,2,5]-thiadiazolo[3,4-d]pyrimidine. The resulting compounds have anticoccidial activity and are useful in controlling cecal and/or intestinal coccidiosis when administered in minor quantities to animals, in particular to poultry usually in admixture with animal sustenance.

2 Claims, No Drawings

PROCESS FOR PREPARATION OF 9-(DIHALOBENZYL)ADENINES

Matter enclosed in heavy brackets [ ] appears in the original patent but forms no part of this reissue specification; matter printed in italics indicates the additions made by reissue.

BACKGROUND OF THE INVENTION

This invention relates to a novel process for preparing 9-(2,6-dihalobenzyl)adenines. Said purines are described in U.S. Pat. No. 3,846,426 as being useful in the treatment and prevention of coccidoisis.

Coccidiosis is a widespread poultry disease which is produced by infections of protozoa of the genus Eimeria which causes severe pathology in the intestines and ceca of poultry. Some of the most significant of these species are E. tenella, E. acervulina, E. necatrix, E. brunetti and E. maxima. This disease is generally spread by the birds picking up the infectious organism in droppings on contaminated litter or ground, or by way of food drinking water. The disease is manifested by hemorrhage, accumulation of blood in the ceca, passage of blood in the droppings, weakness and digestive disturbances. The disease often terminates in the death of the animal, but the fowl which survive severe infections have had their market value substantially reduced as a result of the infection. Coccidiosis is, therefore, a disease of great economic importance and extensive work has been done to find new and improved methods for controlling and treating coccidial infections in poultry.

9-(dihalobenzyl)adenines have been prepared by alkylating adenine with dihalobenzyl halides. This process suffers from the disadvantage that alkylation is not selective and substitution occurs to some extent at the 3-position and other positions of adenine.

E. C. Taylor, et al., J. Org. Chem. 36, 3211 (1971) have reported that 9-substituted adenines (2) may be prepared via reductive cleavage and subsequent cyclization of 7-amidofurazano[3,4-d]pyrimidines (1).

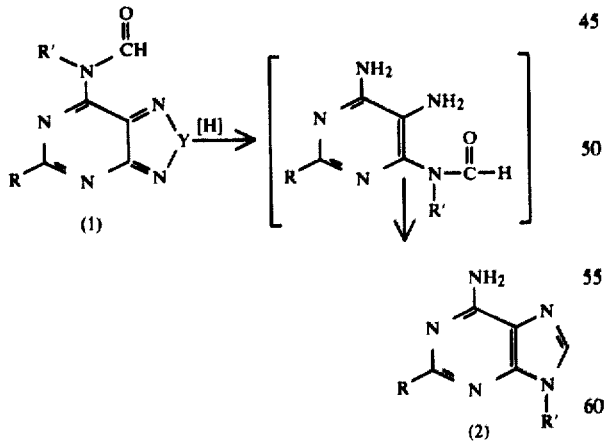

Although a wide variety of adenine derivatives was prepared, the authors were unable to effect the conversion of 5-unsubstituted 7-amidofurazano[3,4-d]pyrimidines (1, R=H, Y=O) to 2-unsubstituted adenines (2, R=H) due to the hydrolytic instability of the former compounds.

According to the process of the present invention this conversion has been successfully performed in the case wherein in compound (1) R=H, Y=S and R'= dihalobenzyl to provide 9-(dihalobenzyl)adenines (2) wherein R=H and R'= dihalobenzyl uncontaminated with positional isomers.

SUMMARY OF THE INVENTION

According to the process of the present invention 9-(dihalobenzyl)adenines, unsubstituted at the 2-position, are prepared without isomer contamination according to the process set forth in Table I.

TABLE I

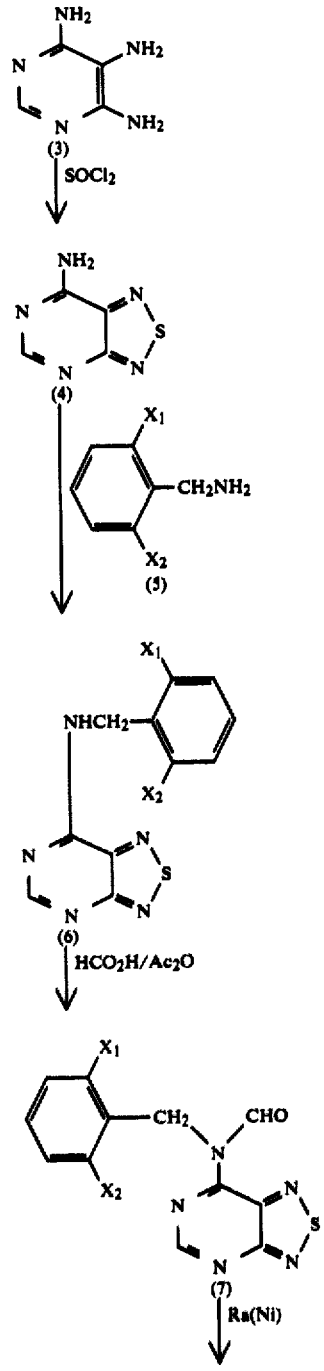

TABLE I-continued

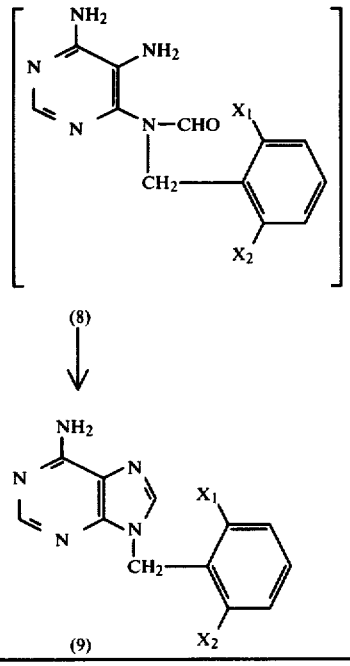

wherein $X_1$ and $X_2$ are independently halogen.

4,5,6-Triaminopyrimidine (3), obtained by the process set forth in A. Shrage et al., J. Org. Chem., 16, 207 (1951), with thionyl chloride affords 7-amino[1,2,5]-thiadiazolo[3,4-d]pyrimidine (4). Nucleophilic displacement of the 7-amino group of (4) by the process of Y. F. Shealy et al., J. Org. Chem., 27, 2135 (1964), at 100° C. with 2,6-dihalobenzylamine (5) provides (6). Alternatively, (6) can be prepared from (4) by treatment of (4) with ammonia and 2,6-dihalobenzyl chloride in a sealed vessel at 100° C. Formylation of (6) at room temperature with formic acetic anhydride yields (7) as a stable solid. Treatment of a solution of (7) with Raney nickel results in smooth desulfurization and formation of (9). The desulfurization may be carried out in an aqueous alcohol solvent wherein the alcohol preferably contains 1 to 6 carbon atoms. The reaction may be conducted at a temperature range of about room temperature to about 125° C. for a period of about 1 hour to 24 hours. Preferred conditions are ethanol-water at about room temperature for about 2 hours.

The present process may be extended to prepare adenine derivatives having the following structure:

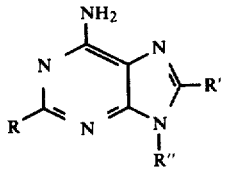

wherein R and R' are independently H, alkyl, aryl or substituted aryl; and R'' is alkyl or substituted benzyl. The substituents are those stable to Raney nickel reduction.

Included within the scope of the present invention are the intermediates useful for the preparation of anticoccidial agents having the structural formula:

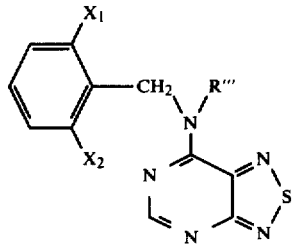

wherein $X_1$ and $X_2$ are independently halogen and R''' is H or CHO.

The following non-limiting Examples will serve to further illustrate the instant invention.

EXAMPLE 1

Preparation of 7-Amino[1,2,5]thiadiazolo[3,4-d]pyrimidine

A flask was charged with 19.78 g. (0.15 mole) of 4,5,6-triaminopyrimidine and 163.0 g. (137 mole) of thionyl chloride and the mixture stirred at reflux for 18 hours. The dark orange reaction mixture was evaporated to dryness on the rotary evaporator and to the residue was added 500 ml. water and 40 ml. methanol. The resulting solution was adjusted to a pH of 7.5–8.0 with saturated sodium bicarbonate solution and heated to reflux. The hot mixture was filtered and the filtrate cooled to 0°–5° C. in an ice-bath. The solid was collected by filtration, washed twice with 50 ml. ice water and twice with 50 ml. ether. The resulting tan product was dried in vacuo at 70° C. overnight to afford 18.2 g. (79%) of product. M.p. 247°–249° C.; tlc on silica gel in chloroform-methanol (8:1) showed one spot at $R_f$=0.4.

EXAMPLE 2

Preparation of 2-Chloro-6-fluorobenzylamine

An autoclave was charged with 89.0 g. (0.5 mole) of 2-chloro-6-fluorobenzyl chloride, 170.0 g. (10 mole) ammonia and 50 ml. benzene. The reaction vessel was sealed and the contents heated at 100° C. for 15 hours. The excess ammonia was carefully evaporated off from the cooled contents of the autoclave with a stream of nitrogen. The residue was washed with water, and the organic phase after drying with anhydrous $MgSO_4$, fractionated to afford 72.4 g. (90%) of product as a clear liquid; b.p. 99°–100° C./20 mm; NMR ($CDCl_3$) δ 1.46 (s, 2H); 3.88 (d, 2H); 7.00 (m, 3H).

EXAMPLE 3

Preparation of 7-(2-Chloro-6-fluorobenzylamino)[1,2,5]-thiadiazolo[3,4-d]pyrimidine A flask was charged with 1.54 g. (0.01 mole) of 7-amino[1,2,5]thiadiazolo[3,4-d]pyrimidine prepared by the process set forth in Example 1 and 4.0 g. (0.025 mole) of 2-chloro-6-fluorobenzylamine prepared by the process set forth in Example 2. The suspension was stirred and heated at 105° C. for 18 hours. Ten ml. water and 20 ml. hexane were added in one portion and the resulting solid collected by filtration. The cake was washed with hexane and dried at 50° C. in vacuo to afford 2.86 g. (97%) of product. M.p. 224°–226° C.; tlc on silica gel in chloroform-methanol (8:1) showed a single fluorescent blue spot at $R_f$=0.8; NMR (DMSO- $d_6$) δ 4.92 (2H, s); 7.21 (broad s, 3H); 8.44 (s, 1H); 9.45 (s, 1H).

Elemental analysis calculated for $C_{11}H_7ClFN_5S$: Calculated: C, 44.68; H, 2.38; N, 23.68. Found: C, 44.36; H, 2.38; N, 24.24.

EXAMPLE 4

Preparation of 7-(2-Chloro-6-fluorobenzylamino)[1,2,5]-thiadiazolo[3,4,-d]pyrimidine An autoclave was charged with 1.54 g. (0.01 mole) of 7-amino[1,2,5]thiadiazolo[3,4-d]pyrimidine prepared by the process set forth in Example 1, 5.1 g. (0.3 mole) ammonia and 4.48 g. (0.025 mole) 2-chloro-6-fluorobenzyl chloride. The vessel was sealed and the contents heated at 110° C. for 15 hours. After cooling and evaporation of the excess ammonia, the resulting solid was collected by filtration, washed successively with water and hexane to afford a 25% yield of product.

EXAMPLE 5

Preparation of 7-(N-formyl-N-2-chloro-6-fluorobenzyl)amino[1,2,5]-thiadiazolo[3,4-d]pyrimidine Formic acetic anhydride was prepared by stirring for 1 hour at 0°-5° C. a solution of 18.4 g. (0.4 mole) of 98% formic acid and 40.8 g. (0.4 mole) acetic anhydride. Forty ml. of this solution was added to 2.0 g. (0.0067 mole) of 7-(2-chloro-6-fluorobenzylamino) [1,2,5]thiadiazolo[3,4-d]pyrimidine prepared by the process set forth in Example 3, and the solution stirred overnight. Any insoluble material was filtered off and the filtrate concentrated in vacuo at 50° C. The solid residue was washed with ether and recrystallized from methanol to afford 2.0 g. (91%) of the desired compound. M.p. 133°-135° C.; tlc on silica gel in chloroform-methanol (16:1) showed one spot with $R_f$=0.8; ir($CHCl_3$) 1730, 1540, 1120, 940 $cm^{-1}$; NMR (DMSO-$d_6$) δ 5.55 (s, 2H); 7.30 (broad s, 3H); 911 (s, 1H); 1033 (s, 1H).

EXAMPLE 6

Preparation of 9-(2-Chloro-6-fluorobenzyl)adenine

A flask was charged with 0.5 g. (0.0016 mole) of 7-(N-formyl-N-2-chloro-6-fluorobenzyl)amino[1,2,5]-thiadiazolo[3,4-d]pyrimidine prepared by the process set forth in Example 5, 15 ml. ethanol, 15 ml. water and 7.0 g. of Raney nickel. The dark suspension was stirred at room temperature for 2 hours at which time tlc analysis showed the reaction to be complete. The reaction mixture was filtered through celite and the cake was washed with 200 ml. of boiling methanol. The clear filtrate was concentrated in vacuo to afford a while solid residue which was recrystallized from methanol-water to afford 0.18 g. (40%) of product. M.p. 245°-246° C.; tlc on silica gel in chloroform-methanol (16:1) showed one spot with $R_f$=0.4; NMR (acetic acid-$d_4$) δ 5.70 (2H, d); 7.35 (3H, m); 8.15 (1H, s).

Elemental analysis calculated for $C_{12}H_9ClFN_5$: Calculated: C, 51.90; H, 3.27; N, 25.22; Cl, 12.77. Found: C, 51.77; H, 3.30; N, 25.43; Cl, 12.49.

What is claimed is:

1. The process for the preparation of compounds having the structure:

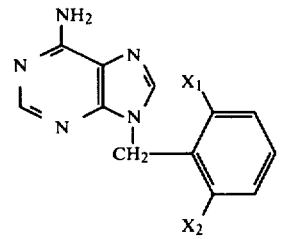

wherein $X_1$ and $X_2$ are independently halogen by reacting the compound having the structure:

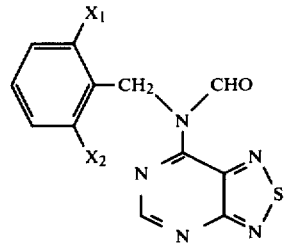

wherein $X_1$ and $X_2$ are as defined above with Raney nickel in aqueous-alcohol solvent at about room temperature to about 125° C. for a period of about 1 hour to 24 hours.

*2. The compound 9-(2-chloro-6-fluorobenzyl)adenine free of 3-position isomers such that said compound has a melting point of 245°-246° C.; a thin layer chromatogram on silica gel in chloroform-methanol (16:1) showing one spot with an Rf of 0.4; and a nuclear magnetic resonance spectrum in acetic acid-d4 of δ 5.70 (2 hydrogens-doublet), δ 7.35 (3 hydrogens-multiplet, and δ 8.15 (1 hydrogen-singlet).*

* * * * *